(12) United States Patent
De Vos et al.

(10) Patent No.: US 12,029,540 B2
(45) Date of Patent: Jul. 9, 2024

(54) WEARABLE MEASURING DEVICE THAT CAN BE WORN ON A PERSON'S BODY

(71) Applicant: Monoa BVBA, Dendermonde (BE)

(72) Inventors: Renaat De Vos, Evergem (BE); Stijn Bogaerts, Dendermonde (BE)

(73) Assignee: Monoa BVBA, Dendermonde (BE)

( * ) Notice: Subject to any disclaimer, the term of this patent is extended or adjusted under 35 U.S.C. 154(b) by 595 days.

(21) Appl. No.: 17/286,162

(22) PCT Filed: Oct. 14, 2019

(86) PCT No.: PCT/IB2019/058730
§ 371 (c)(1),
(2) Date: Apr. 16, 2021

(87) PCT Pub. No.: WO2020/079559
PCT Pub. Date: Apr. 23, 2020

(65) Prior Publication Data
US 2021/0386314 A1   Dec. 16, 2021

(30) Foreign Application Priority Data

Oct. 17, 2018   (BE) .................................. 2018/05713

(51) Int. Cl.
*A61B 5/0533*   (2021.01)
*A61B 5/00*   (2006.01)

(52) U.S. Cl.
CPC .......... *A61B 5/0533* (2013.01); *A61B 5/6804* (2013.01); *A61B 5/681* (2013.01); *A61B 5/6831* (2013.01); *A61B 5/6838* (2013.01)

(58) Field of Classification Search
CPC ..... A61B 5/0533; A61B 5/6804; A61B 5/681; A61B 5/6831; A61B 5/6838
See application file for complete search history.

(56) References Cited

U.S. PATENT DOCUMENTS

| | | | |
|---|---|---|---|
| 2004/0039254 A1 | 2/2004 | Stivoric et al. | |
| 2007/0106133 A1* | 5/2007 | Satchwell | G16H 40/67 600/509 |
| 2010/0010565 A1* | 1/2010 | Lichtenstein | A61B 5/318 607/46 |
| 2014/0275888 A1 | 9/2014 | Wegerich et al. | |

(Continued)

FOREIGN PATENT DOCUMENTS

| | | |
|---|---|---|
| WO | 2014/205434 A2 | 12/2014 |
| WO | 2015101947 A2 | 7/2015 |
| WO | 2017165532 A1 | 9/2017 |

OTHER PUBLICATIONS

International Search Report issued Feb. 4, 2020 which pertains to PCT/IB2019/058730 filed Oct. 14, 2019, 4 pages.

*Primary Examiner* — Paula J Stice
(74) *Attorney, Agent, or Firm* — Dinsmore & Shohl LLP

(57) ABSTRACT

A wearable measuring device that can be worn on a person's body, that is intended for measuring parameters on the skin of the person and that is designed as a measuring block equipped with an elongated, shell-shaped housing with a convex side and a concave side and in which the surface of the concave side and wherein the surface of the concave side is equipped with at least a pair of electronic sensors meant to be put into contact with the skin of the person concerned for measuring the parameters.

18 Claims, 13 Drawing Sheets

(56) References Cited

U.S. PATENT DOCUMENTS

| | | |
|---|---|---|
| 2015/0157220 A1* | 6/2015 | Fish .................. A61B 5/681 |
| | | 600/595 |
| 2015/0280763 A1* | 10/2015 | Ko ........................ H02J 7/04 |
| | | 455/73 |
| 2016/0317060 A1 | 11/2016 | Connor |
| 2018/0143663 A1 | 5/2018 | Seok et al. |
| 2018/0288586 A1 | 10/2018 | Tran et al. |
| 2019/0298009 A1* | 10/2019 | Herz .................. A44C 5/0053 |

* cited by examiner

WEARABLE MEASURING DEVICE THAT CAN BE WORN ON A PERSON'S BODY

CROSS-REFERENCE TO RELATED APPLICATIONS

The present application is the National Phase entry of International Patent Application No. PCT/IB2019/058730 filed Oct. 14, 2019, the entire contents of which are hereby incorporated by reference into this application.

TECHNICAL FIELD

The present disclosure concerns a wearable measuring device that can be worn on a person☐s body.

BACKGROUND

The common English terminology in the technical field to which the present disclosure relates includes terms such as 'wearable', 'wearable technology', 'wearable devices', which describe a variety of devices or gadgets that a person wears as a garment or accessory on his or her body and which contain technology to measure, collect and, if necessary, transmit data on the body☐s condition to other devices.

In French, there is also mention of the so-called "habitronique", which is a composition of "s'habiller" (meaning "to dress") and "électronique".

In short, a wearable measuring device according to the present disclosure can be considered as an element that belongs to the technical domain of the aforementioned electronic devices that can be worn by a person on the body.

More specifically, the present disclosure relates to such a wearable measuring device that is intended to measure parameters on the person's skin.

Such parameters can take many forms, but according to the present disclosure will typically (but not necessarily) relate to physical parameters related to the activity of the sweat glands in the skin, such as, for example, the electrical conductivity of the skin, the speed or magnitude at which this conductivity of the skin changes and so on.

Indeed, a change in the activity of the sweat glands reflects a change in the intensity of the emotional state or excitement of the person concerned.

The aim is that a wearable measuring device according to the present disclosure can monitor a person's emotional state, state of mind or excitement and that the data collected by the measuring device can be offered to the person, typically by a separate output device, such as an app on a mobile phone or on any communication device, or by software installed on a PC, laptop or tablet or on any other device that is appropriate.

According to the present state of the art, many electronic devices are known that can be worn on the body by a person (the so-called "wearables"), but a number of needs cannot be met at present with these known devices.

For example, there are the well-known watches with built-in technology (the so-called "smartwatches") for monitoring, for example, sports performances, the heart rate, and so on.

In other words, in this "intelligent" type of watches, the original functions relating to the display of date and time and so on, together with the functions relating to the measurement of data on the person's skin and the storage and monitoring of these data, are integrated into a single device, in this example the watch.

This integration of functions has disadvantages.

More specifically, the makers of technology for measuring data on the skin are not primarily manufacturers of watches and vice versa.

Consequently, the watches with integrated measurement technology in most cases look rather futuristic with a very digital look.

This is mostly not annoying when it comes to sports performances, for example, but when the measurement technology is used for continuous monitoring of the individual's state of mind, it is often undesirable to have to wear a flashy electronic device around the wrist all day long.

This is particularly the case, for example, for persons who are expected to wear more formal clothing at work, such as office workers, salesmen, lawyers, judges and the like.

Another disadvantage of the aforementioned integration of functions is that when buying a watch, there are many models in which the measurement technology is not integrated and only a few models in which this measurement technology is integrated, so that the choice when buying a watch is very limited if, in addition to the time display, one is also looking for technology that is able to measure the emotional state.

Other similar electronic devices or ☐wearables☐ can be glued to the body or may have the shape of a flexible bracelet or the like.

A disadvantage of these electronic devices or "wearables" is again that they are usually very flashy, which is often undesirable for the aforementioned reasons.

Furthermore, they are generally not very durable or robust and are intended rather as a gadget or novelty for temporary experimentation, or for short-term use.

Another disadvantage of these embodiments is that they cover a fairly large part of the skin surface, which can lead to itching, irritation and even infections.

The present disclosure therefore aims to provide a solution to the aforementioned problem and/or other problems.

SUMMARY

In particular, the aim of the present disclosure is to provide a wearable measuring device that is very durable and robust, so that it will have a long service life and can withstand shocks or forces that are commonly exerted by a person in motion, as well as any penetration of moisture into the measuring device.

Another aim of the present disclosure is to provide the technology used to measure a person's skin in one separate wearable measuring device, which may have a very small volume, so that it can be worn discreetly.

Another aim of the present disclosure is to supply a measuring device that a user can wear unnoticed or almost imperceptibly on, in or under his daily clothing or other accessories worn by the user, such as watches, bras or belts, in such a way that the user does not have to change his vestimentary habits and style in any way, and can continue to purchase clothing and accessories from the ordinary wide range of products available on the market, as in the past.

Yet another aim of the present disclosure may be to offer a wearable measuring device that is not only durable, but also exudes a certain standing or is at least designed such that it can also be worn by persons who attach great importance to class and style.

On the other hand, in another possible embodiment, one possible aim of the present disclosure is to provide a durable wearable measuring device with an emphasis on its wide distribution, for example by trying to keep its cost price as low as possible.

To this end, the present disclosure concerns a wearable measuring device that can be worn on a person's body, intended to measure parameters on the person's skin, carried out like a measuring block fitted with an elongated, slightly curved housing, more specifically as if it were a segment of a cylindrical sheath with a radius between 52 and 62 millimetres, between 54 and 60 millimetres, or between 56 and 58 millimetres, with a convex side and a concave side, and having in the surface of the concave side at least two electronic sensors intended to be put into contact with the skin on the inside of the wrist of the person concerned to measure the parameters, wherein the wearable measuring device is not equipped with a wristband or the like.

An aspect of such a wearable measuring device according to the present disclosure is that it has a housing whose concave side can be fitted over a convex part of the skin at the wrist so that a good contact between the skin and the sensors in the wearable measuring device is ensured.

Another aspect of such a wearable measuring device according to the present disclosure is that it is designed as a separate measuring block with a housing in which the electronic sensors are provided.

In this way, a robust and compact version can be realized on the one hand, and the measuring technology is contained in a separate block on the other hand, so that such a measuring block in a particular embodiment can be combined with many types of watches and other wristbands, for example.

In an embodiment of a wearable measuring device according to the present disclosure, the measuring block contains at least a pair of electronic sensors for measuring the activity of the sweat glands in the skin zone concerned, also called ☐galvanic skin response☐, wherein at least two sensors are provided at a mutual distance of at least 20 millimetres and wherein the sensors have a rounded contact surface.

If the distance is long enough, a battery can be fitted between the sensors.

An aspect of such an embodiment of a wearable measuring device in accordance with the present disclosure is that it allows to detect and record the state of mind or more physical parameters such as the heartbeat of the wearer, so that this knowledge can be used at a later stage or simultaneously in all kinds of apps or software programs, for example to improve the general well-being of the person concerned or monitor or preventively adjust his or her general condition.

In yet another embodiment of a measuring device according to the present disclosure, the wearable measuring block is designed to be attached to a wristband, for example of a usual wristwatch, in particular to be used between the wristband and the skin on the inside of the wrist and it is provided with a fixing member to this end.

An aspect of such an embodiment of a wearable measuring device according to the present disclosure is that the garment or accessory such as a watch to which it is attached ensure a good contact with the user's skin.

The wearable measuring device is adapted to the watch or wristband, but any embodiment of the intended type can serve to attach such a wearable measuring device to it, regardless of the style or detailed shape or colour it has.

This increases the choice of style and shape for a user enormously.

Because the wearable measuring device is attached to a wristband, possibly of a conventional watch, it does not have its own structure of applying it to the user's body, which makes it relatively small in size and allows it to be discreetly applied to the body for measuring the relevant parameters.

In another embodiment of a wearable measuring device according to the present disclosure, the wearable measuring device is equipped with transmitting devices to wirelessly transmit data to an output device, such as a mobile phone, a communication device in general, a PC, laptop, iPod, mp3 player or the like.

The present disclosure also concerns a combination of a wearable measuring device according to the present disclosure and an output device, wherein the output device is equipped with techniques for receiving data from the measuring device wirelessly and with an app or software application capable of processing said data and of presenting it to a user in a processed form.

BRIEF DESCRIPTION OF THE DRAWINGS

In order to better explain the characteristics of the present disclosure, some embodiments of a wearable measuring device according to the present disclosure are described below as an example only without being limitative in any way, with reference to the attached figures in which.

DETAILED DESCRIPTION

Figure 1:
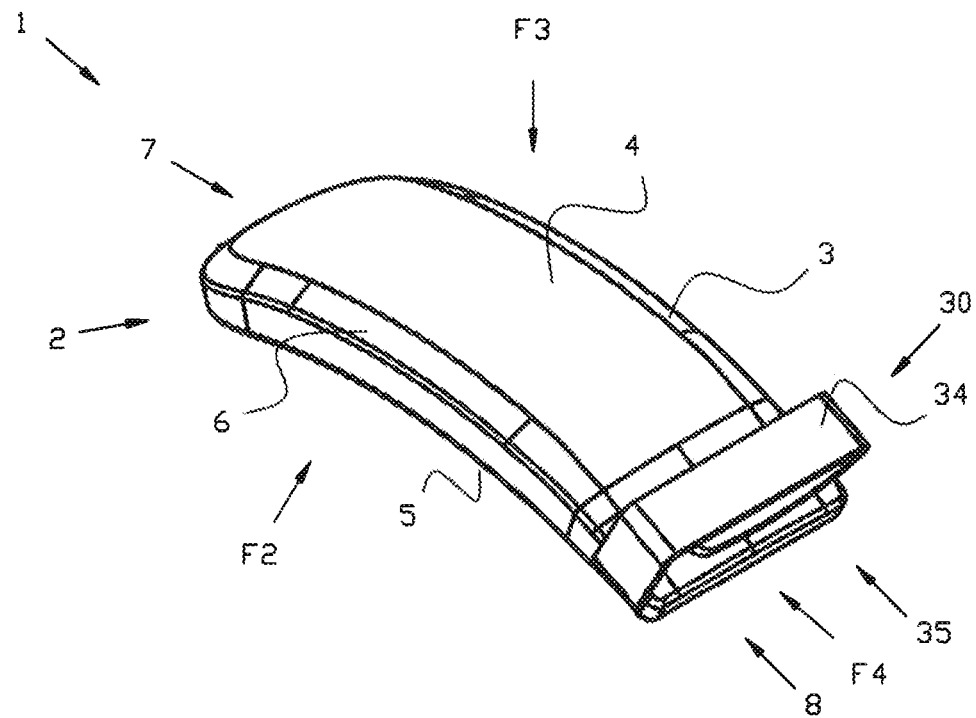
FIG. 1 shows a perspective view of a convex side of a first embodiment of a wearable measuring device according to the present disclosure.

The wearable measuring device 1 according to the present disclosure shown in FIGS. 1 to 7 included is intended to measure parameters on a user☐s skin 11.

The wearable measuring device 1 is designed as a closed unit in the shape of a measuring block 2 that is equipped with an elongated, shell-shaped housing 3.

This housing 3 has a convex side 4 and a concave side 5.

In addition, the shell-shaped housing 3 has a constant or nearly constant width B and a constant or nearly constant thickness D over the greater part of its length L.

For example, the length L may typically be between 50 and 60 mm, but the present disclosure does not rule out the possibility of using a different length L.

The width B corresponds to the width of a watch strap 31 and may, for example, be in the order of magnitude of 16 mm to 24 mm, but other dimensions are not excluded from the present disclosure.

In some embodiments, the thickness D may be as thin as possible so that the wearable measuring device 1 can be discretely fitted between the watch strap 31 worn by the user and the user's skin.

For example, the thickness D may typically be 6 to 7 mm over a greater part of a surface of the wearable measuring device 1. Of course, thinner as well as thicker versions are not excluded from the present disclosure.

At edges 6, the wearable measuring device 1 in this example is slightly rounded or chamfered and the thickness D slightly decreases, for example to about 4 to 5 mm.

Of course, these values are merely possible examples and, according to the present disclosure, it is not excluded to use completely different shapes and sizes.

In the embodiment shown in FIGS. 1 to 7, the wearable measuring device 1 is provided with a front side 7 that is semi-circular or almost semi-circular and a back side 8 that in this case is rectilinear or almost rectilinear, but according to the present disclosure this does not have to be the case.

Figure 8:
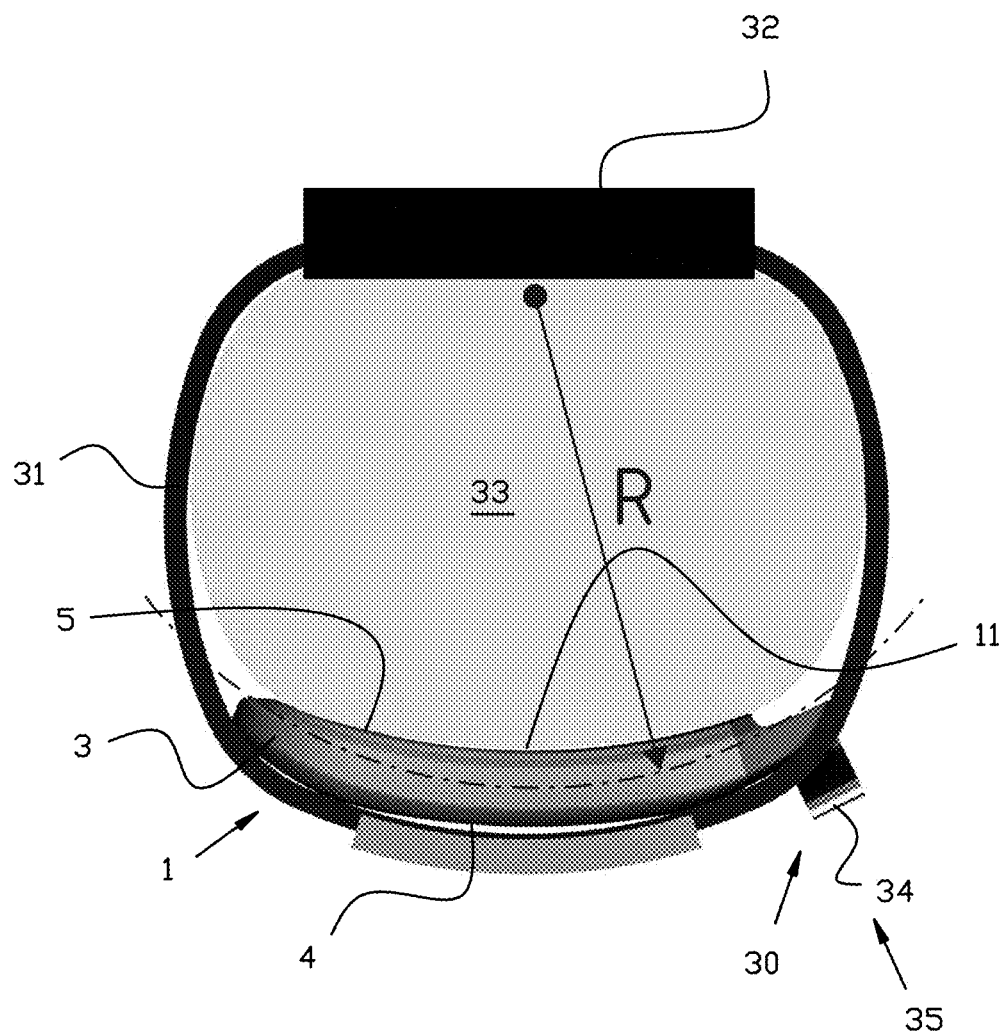
FIG. 8 shows a side view illustrating the use of the wearable measuring device from FIG. 1.
Figure 9:
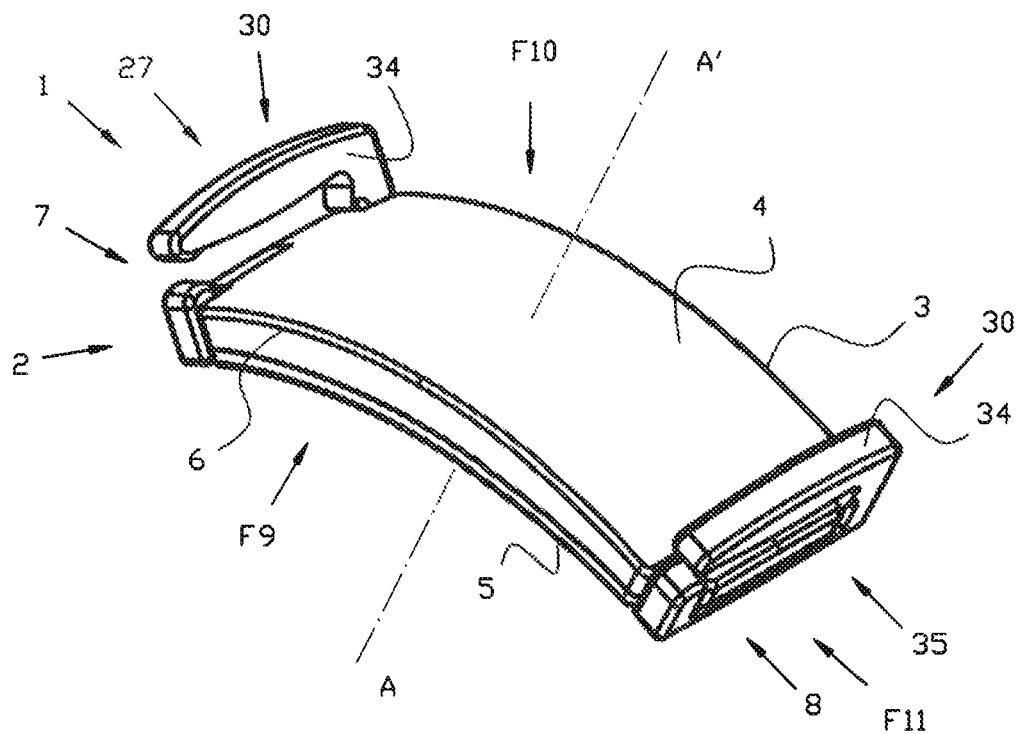
FIG. 9 shows a perspective view of a convex side of a second embodiment of a wearable measuring device according to the present disclosure.
Figure 10:
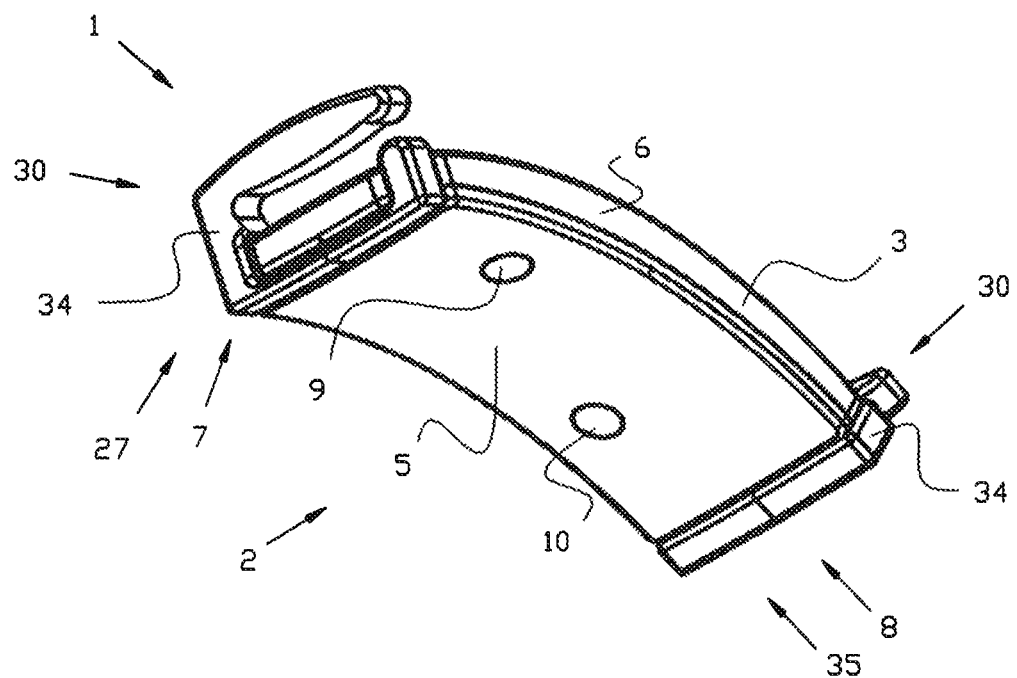
FIG. 10 shows a perspective view according to arrow F9 on a concave side of the wearable measuring device in FIG. 9.
Figure 11:
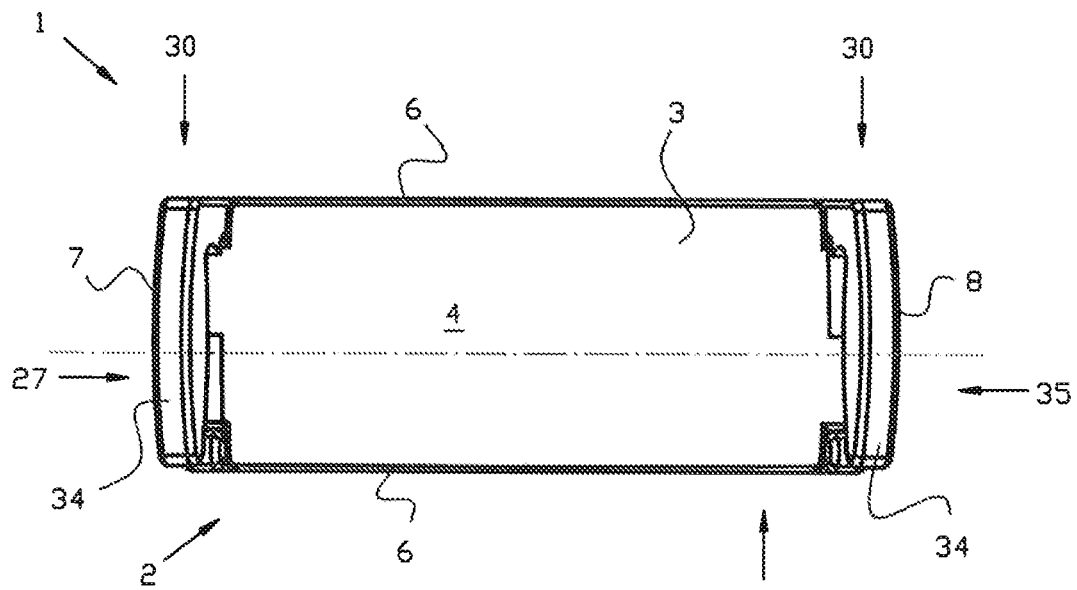
FIG. 11 shows a top view according to arrow F10 on the wearable measuring device from FIG. 9.
Figure 12:
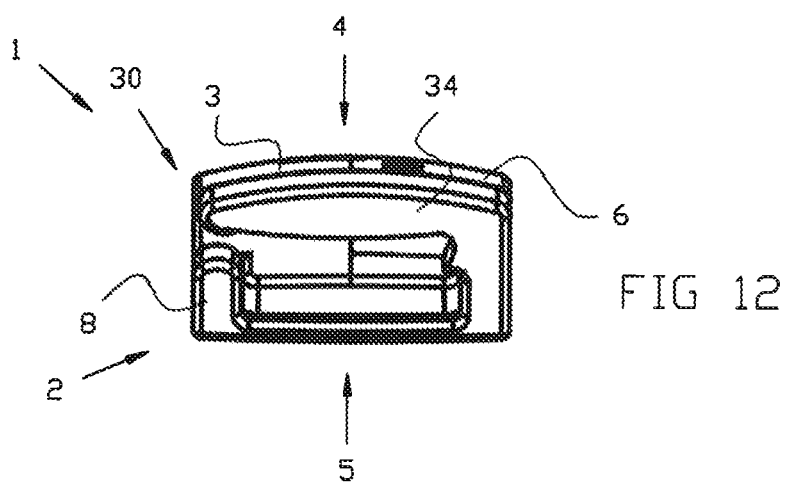
FIG. 12 shows a first side view according to arrow F11 on the wearable measuring device from FIG. 9.
Figure 13:
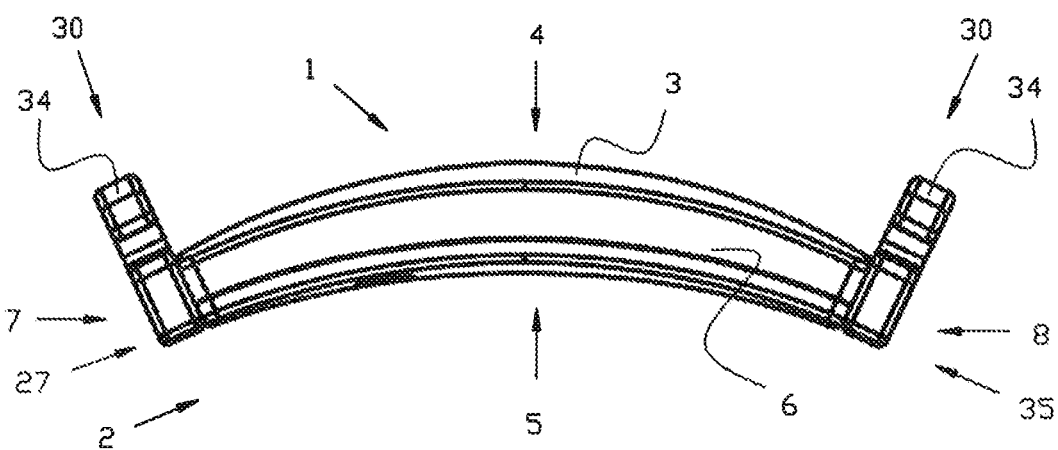
FIG. 13 shows a second side view according to arrow F13 on the wearable measuring device from FIG. 11.

In the surface of the concave side 5, according to the present disclosure, at least a pair of electronic sensors 9 and 10 are provided, which are intended to be brought into contact with a user's skin 11 for measuring the aforementioned parameters, as shown in FIG. 8.

According to the present disclosure, this pair of electronic sensors 9 and 10 is provided in the measuring block 2 typically intended to measure the activity of the sweat glands in the relevant part of the skin 11.

In order to know this activity, the so-called ☐galvanic skin response☐ can be measured, wherein parameters such as, for example, the electrical conductivity on the skin 11 or changes in this electrical conductivity are measured.

However, the present disclosure does not rule out the possibility of measuring other parameters additionally or alternatively, by providing sensors of a different nature or by increasing or decreasing the number of sensors.

In some embodiments, the electronic sensors 9 and 10 may be situated at a sufficient intermediate distance E, for example at a distance E of approximately 2 cm, but other intermediate distances E can also be used.

Figure 6:
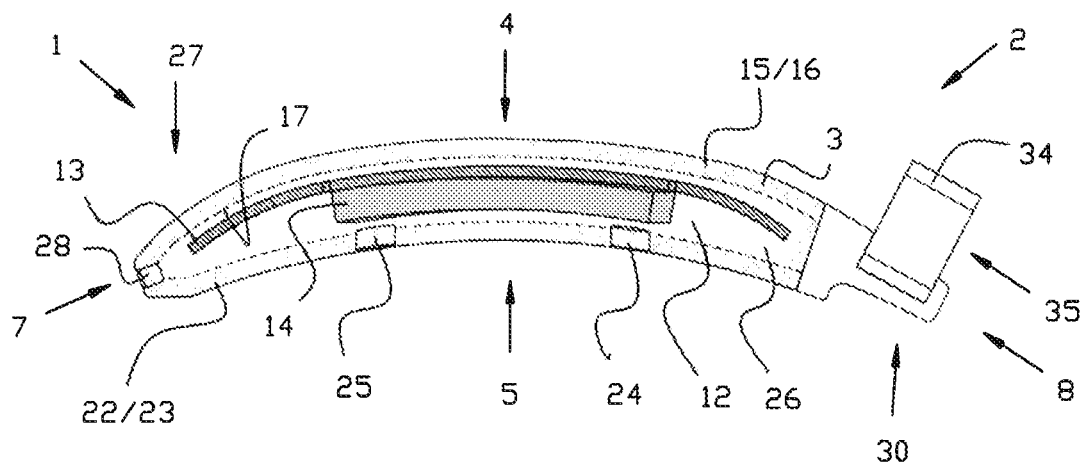
FIG. 6 shows a cross-section view through the wearable measuring device according to the section VI-VI indicated in FIG. 3.
Figure 7:
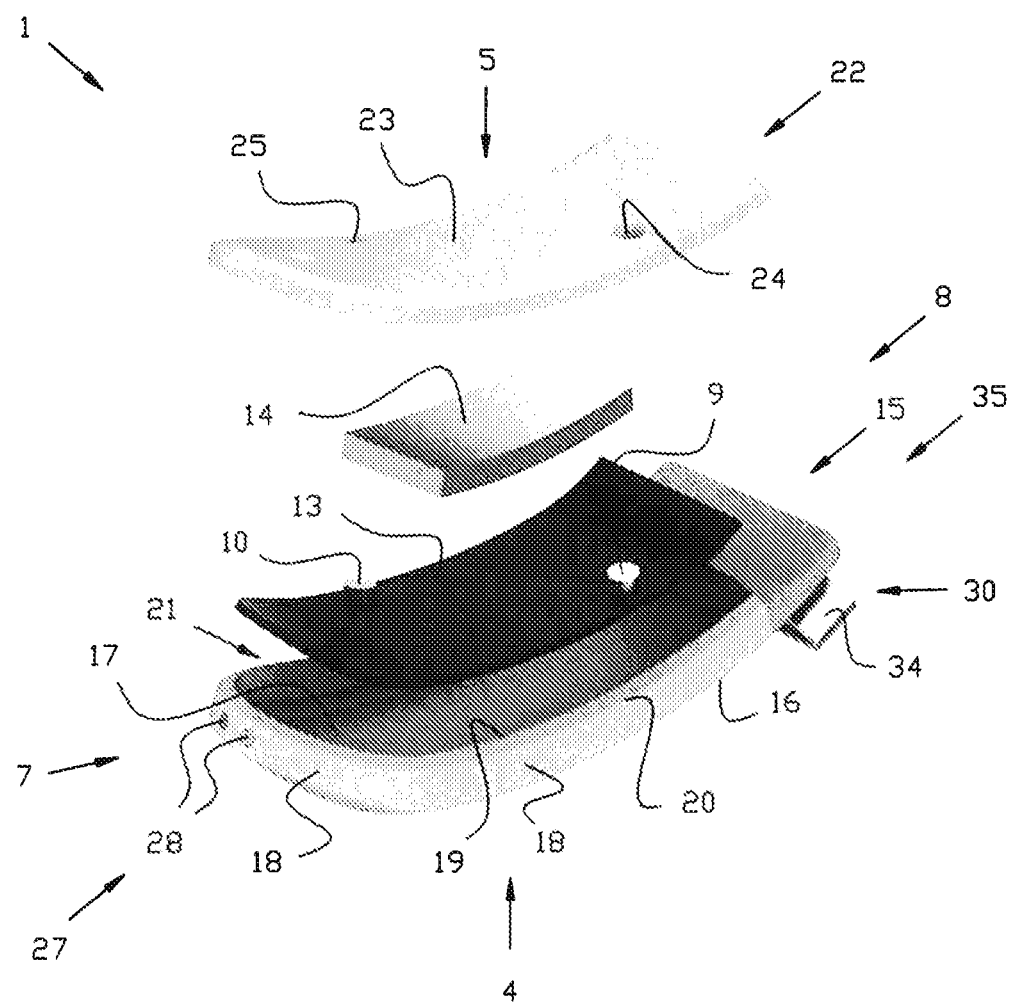
FIG. 7 shows a disassembled perspective view of the wearable measuring device from FIG. 1.

As shown in more detail in FIGS. 6 and 7, the shell-shaped housing 3 of the wearable measuring device 1 encloses an internal space or cavity 12 for housing a printed circuit board (PCB) 13 and a battery 14.

In this case, a first part 15 of the housing 3, i.e. the part that contains the convex side 4, forms a tub-shaped element 16.

The convex side 4 of the housing 3 forms a bottom 17 of the tub-shaped element 16 and is surrounded by upright side walls 18.

Edges 19 at a top 20 of these upright side walls 18 enclose an opening 21.

A second part 22 of the housing 3 has the shape of a concave lid 23 that can be fitted into the opening 21 mentioned above.

The sensors 9 and 10 are mounted on the PCB 13, and holes 24 and 25 are provided in the above-mentioned concave lid 23 for the sensors 9 and 10.

Figure 2:
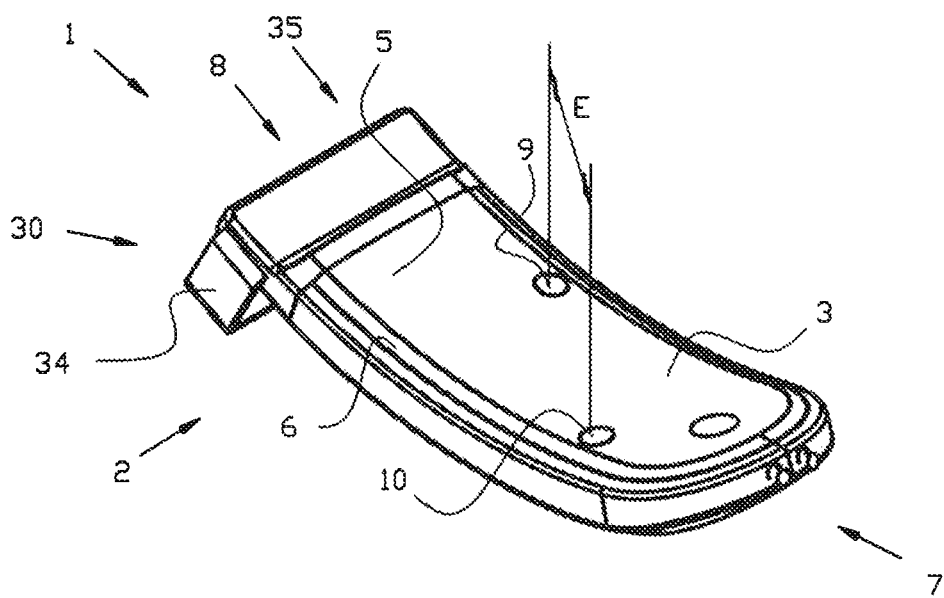
FIG. 2 shows a perspective view according to arrow F2 on a concave side of the wearable measuring device in FIG. 1.
Figure 3:
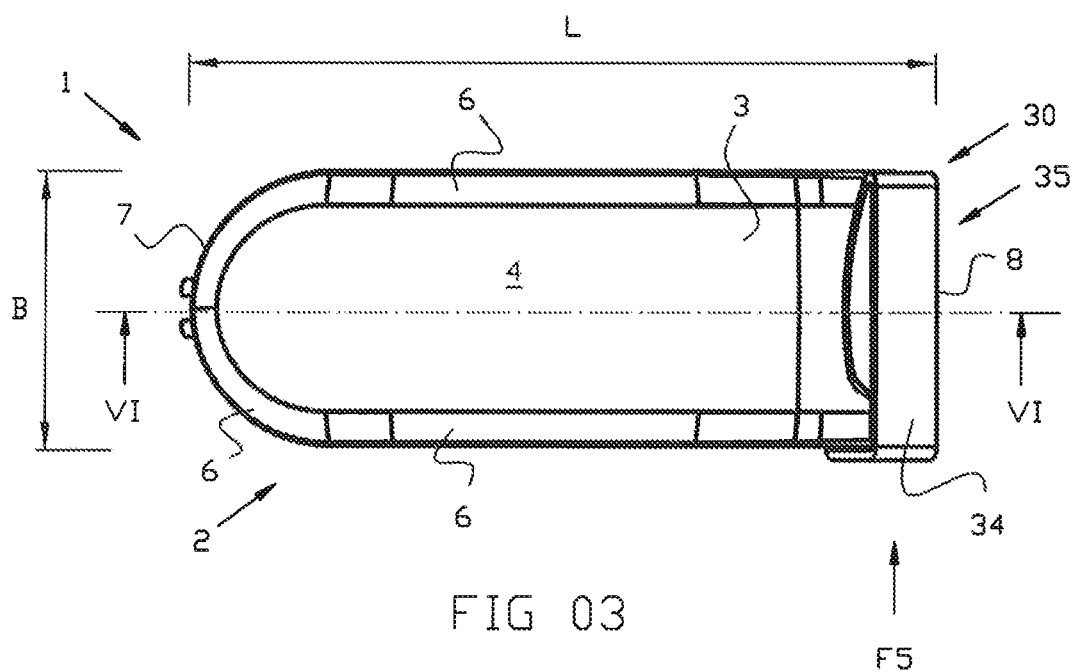
FIG. 3 shows a top view according to arrow F3 on the wearable measuring device from FIG. 1.
Figure 4:
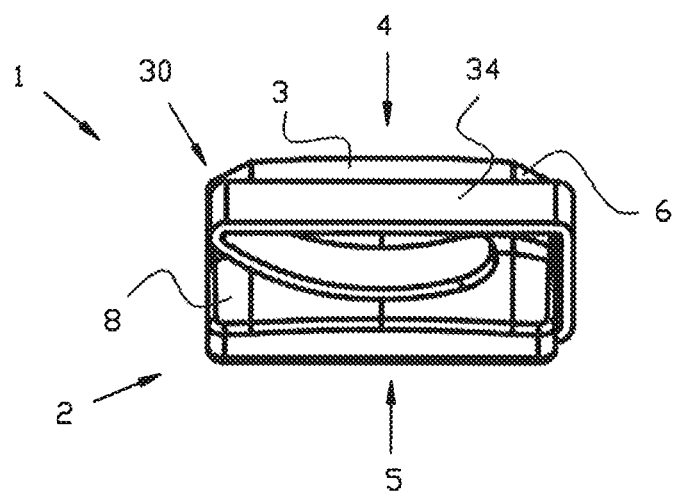
FIG. 4 shows a first side view according to arrow F4 on the wearable measuring device from FIG. 1.
Figure 5:
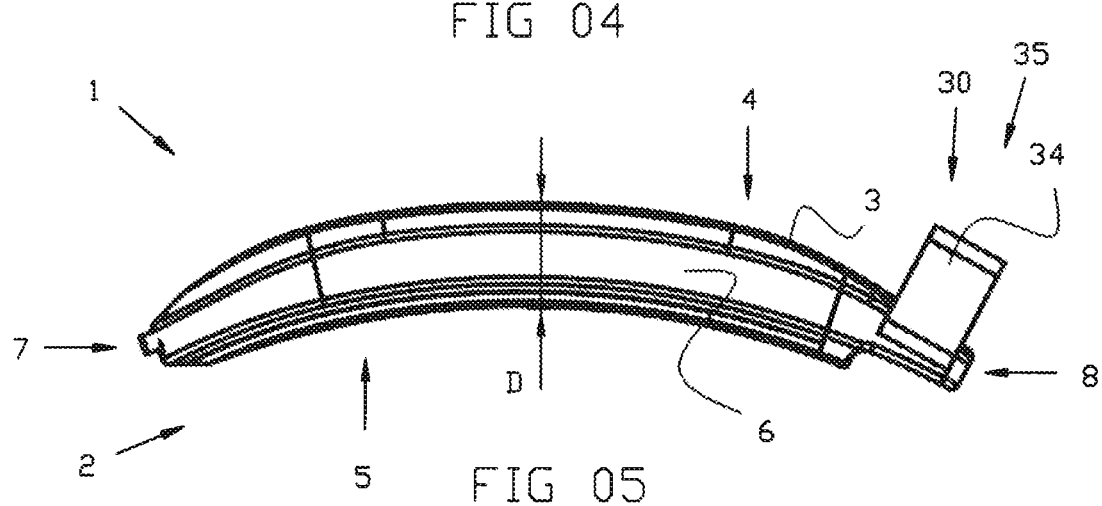
FIG. 5 shows a second side view according to arrow F5 on the wearable measuring device from FIG. 3.

After the introduction of the sensors 9 and 10 in these holes 24 and 25, a head of each sensor 9 and 10 will be situated in a plane of the concave side 5, which is clearly shown in FIG. 2.

In one embodiment, the printed circuit board (PCB) 13, which is provided in the shell-shaped housing 3, is made flexible in such a way that it can be easily adapted to the shell shape of the housing 3.

Another aspect of the present disclosure is that the battery 14, just as the housing 3, is shell-shaped, so that this battery 14 can be easily inserted in the internal space or cavity 12 in the housing 3.

In yet another embodiment of a wearable measuring device 1 according to the present disclosure is further provided a resin 26 in the internal space or cavity 12 in the shell-shaped housing 3, at least in the part thereof that is not filled with electronic or electrical components, such as the battery 14 and the PCB 13 or any other elements.

In some embodiments, two electrical contacts 28 are provided on one longitudinal free end 27 of the housing 3 to charge the battery 14 inside the housing 3. The housing 3 also includes another longitudinal free end 35.

In the embodiment shown in FIGS. 1 to 7, these electrical contacts 28 are provided on the front side 7 of the housing 3.

Figure 27:
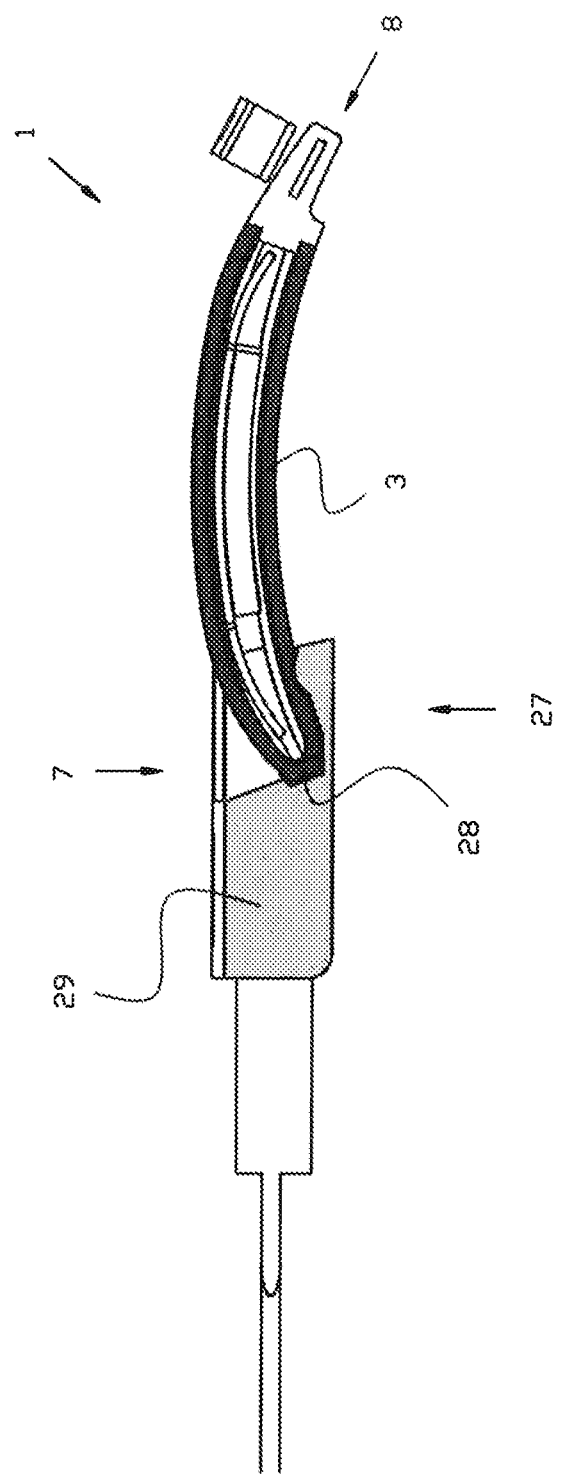
FIG. 27 shows a side view illustrating a charging of the wearable measuring device according to the present disclose in an embodiment as shown in FIG. 1.

Thus, the wearable measuring device 1 can be charged in a battery charger 29 by resting it with the front side 7 in this battery charger 29, which is illustrated by way of example in FIG. 27.

However, according to the present disclosure, it is not excluded for electrical contacts 28 to be provided in other places and for the battery charger 29 to be modified accordingly.

Another aspect of the present disclosure is that the wearable measuring device 1 or measuring block 2 is intended to be attached to the user's garment or to an accessory worn by the user, such as a watch, bra or belt or the like.

For this purpose, the wearable measuring device 1 is equipped with fixing member 30.

In the embodiment of FIGS. 1 to 8 included, the wearable measuring device 1 is intended to be attached to the watch strap 31 of the watch 32 worn around the user's wrist 33.

In this case, the above-mentioned fixing member 30 are carried out as a hook or clips 34 that can be hooked behind or around a part of the garment or accessory in question, in this case behind the watch strap 31.

This is illustrated in FIG. 8.

The hook or clips 34 extend upwards in this case in a direction away from the convex side 4.

It is clear that in this case the fixing member 30 are such that the wearable measuring device 1, after it has been applied, is situated between the watch strap 31 and the user☐s skin 11, with the electronic sensors 9 and 10 on the concave side 5 being pressed or held against the skin 11.

In such an embodiment, the wearable measuring device 1 is very discreetly positioned while wearing it and is hidden between the watch strap 31 and the skin 11.

FIGS. 9 to 13 show a second embodiment of a wearable measuring device 1 according to the present disclosure.

Figure 14:
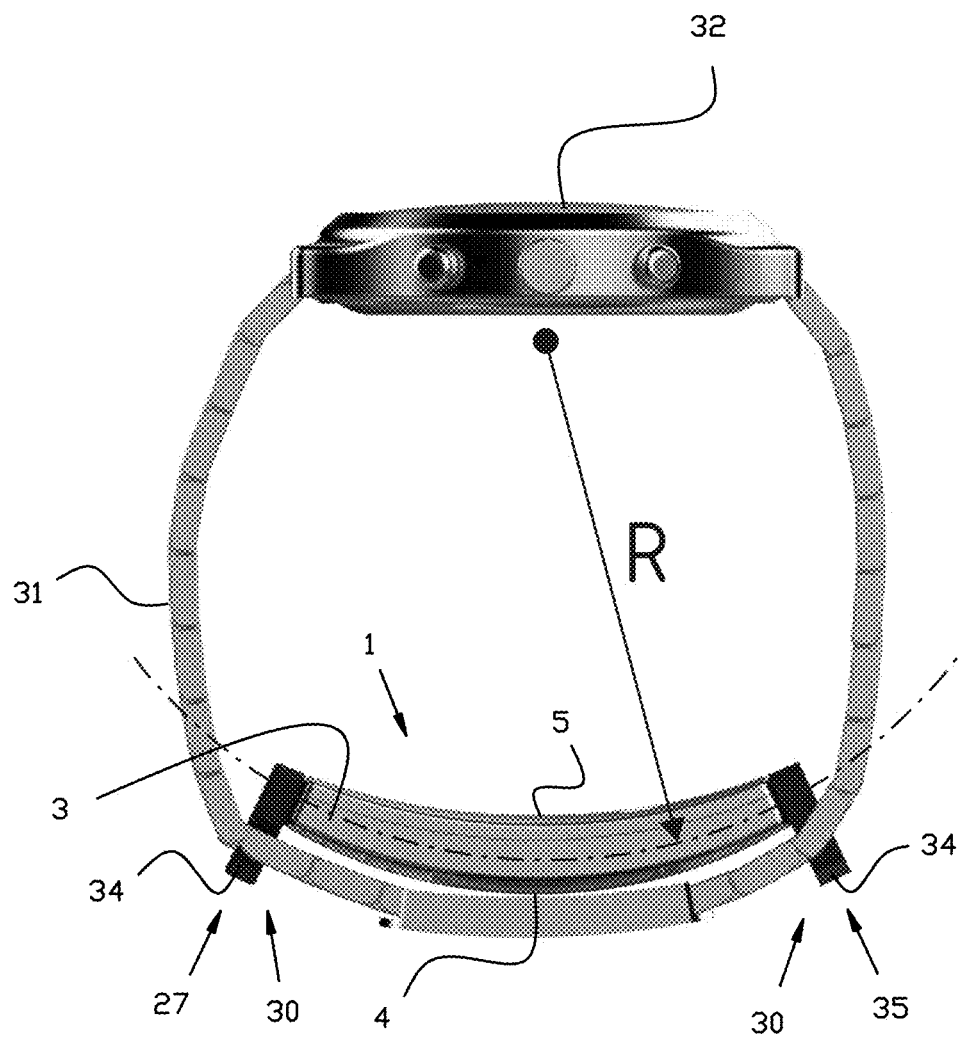
FIG. 14 shows a side view illustrating the use of the wearable measuring device in the embodiment according to FIG. 9.
Figure 15:
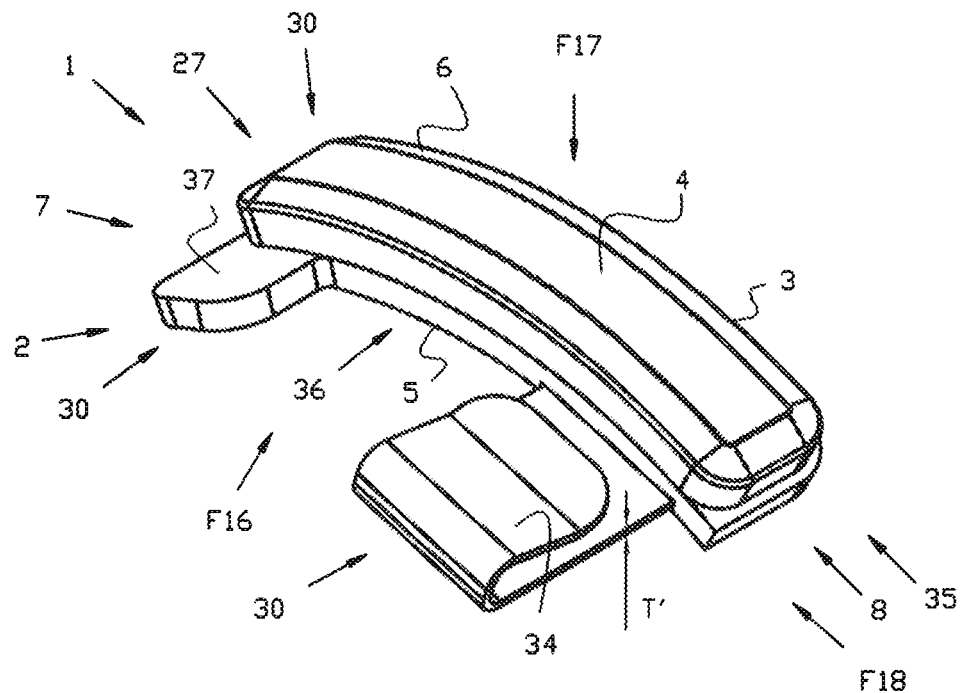
FIG. 15 shows a perspective view of a convex side of a third embodiment of a wearable measuring device according to the present disclosure.
Figure 16:
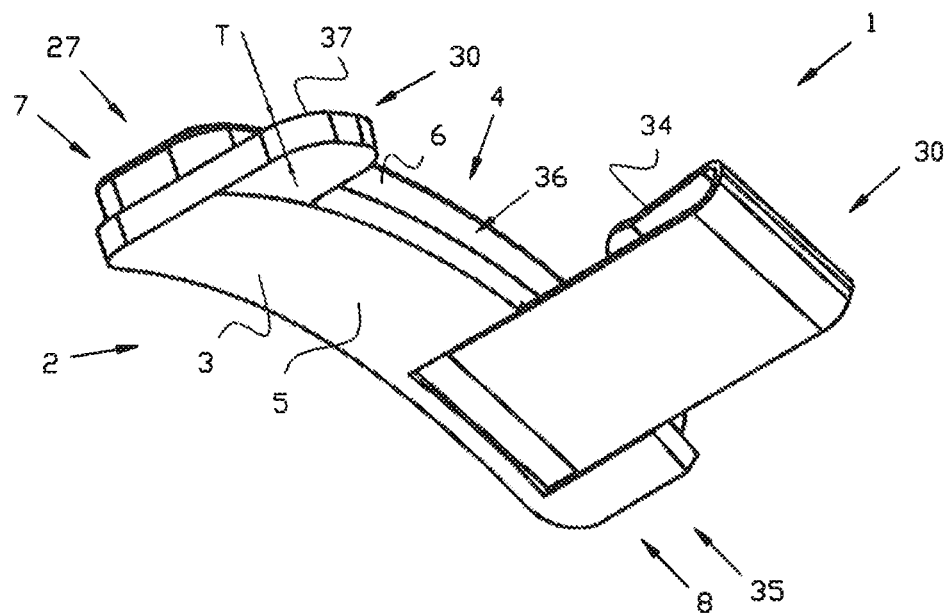
FIG. 16 shows a perspective view according to arrow F16 on a concave side of the wearable measuring device in FIG. 15.
Figure 17:
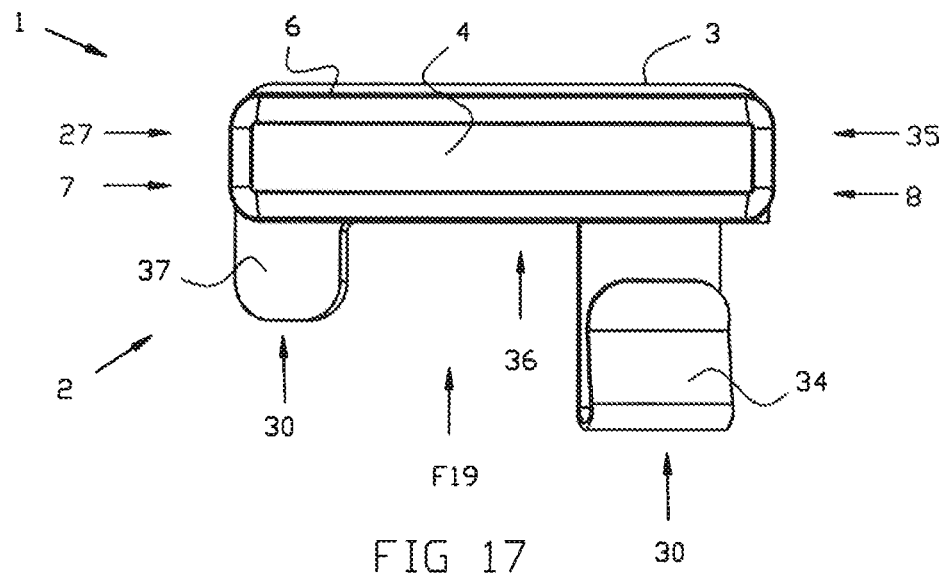
FIG. 17 shows a top view according to arrow F17 on the wearable measuring device from FIG. 15.
Figure 18:
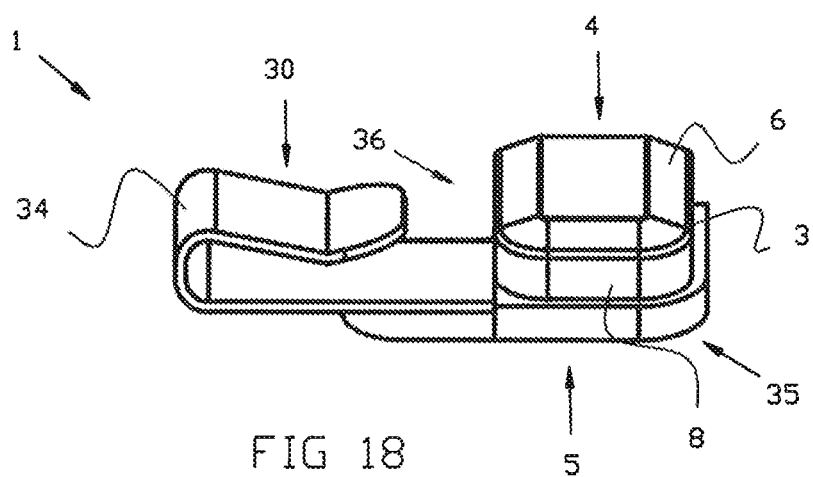
FIG. 18 shows a first side view according to arrow F18 on the wearable measuring device from FIG. 15.
Figure 19:
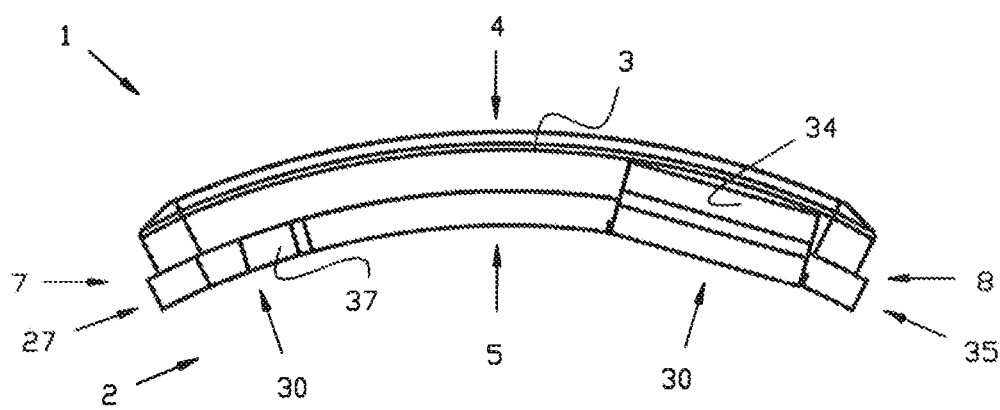
FIG. 19 shows a second side view according to arrow F19 on the wearable measuring device from FIG. 17.
Figure 20:
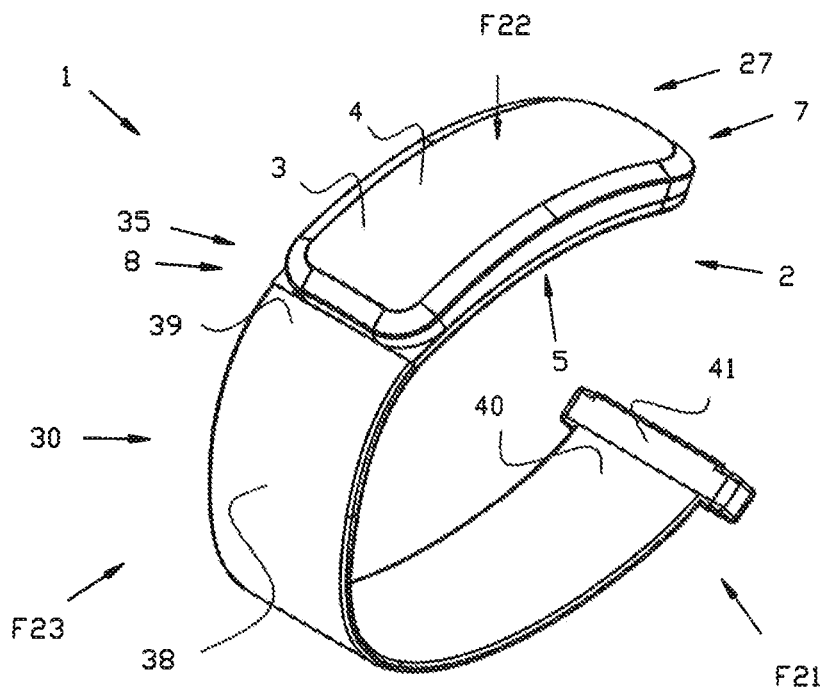
FIG. 20 shows a perspective view in of a convex side of a fourth embodiment of a wearable measuring device according to the present disclosure.
Figure 21:
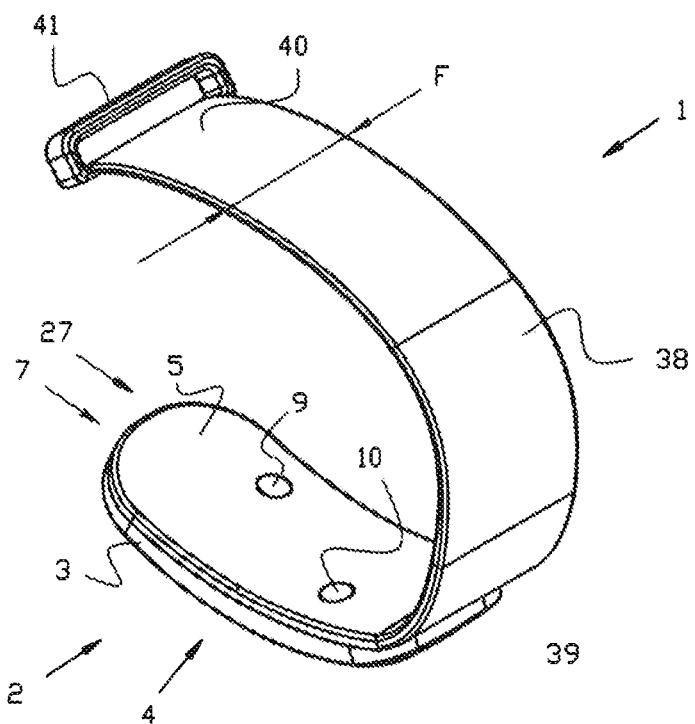
FIG. 21 shows a perspective view according to arrow F21 on a concave side of the wearable measuring device in FIG. 20.
Figure 22:
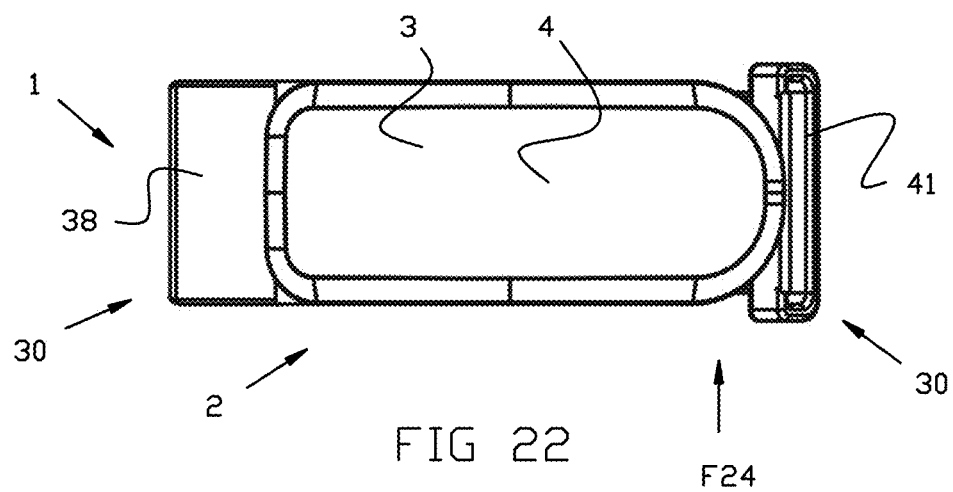
FIG. 22 shows a top view according to arrow F22 on the wearable measuring device from FIG. 20.
Figure 23:
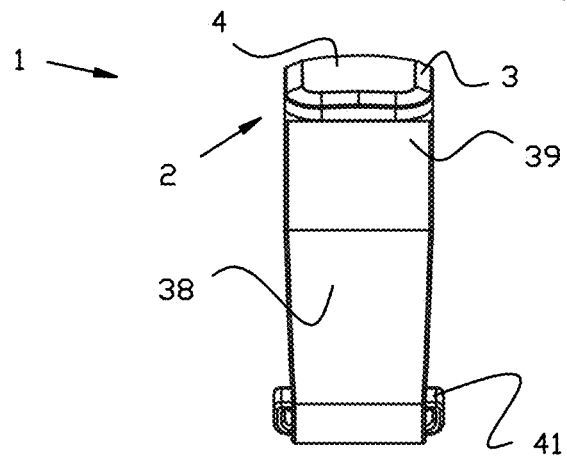
FIG. 23 shows a first side view according to arrow F23 on the wearable measuring device from FIG. 20.
Figure 24:
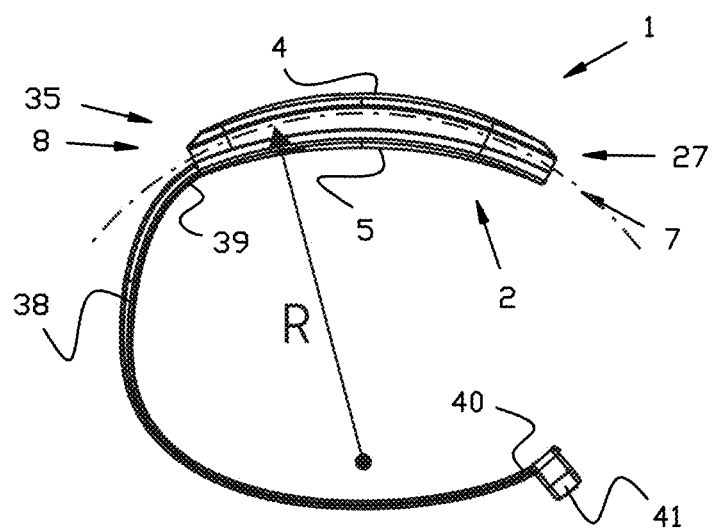
FIG. 24 shows a second side view according to arrow F24 on the wearable measuring device from FIG. 22.

Just as in the first embodiment, this wearable measuring device 1 is intended to be attached to the watch strap 31 of the watch 32, wherein the wearable measuring device 1 is also placed between the watch strap 31 and the skin 11, which is illustrated in FIG. 14.

The difference with the first embodiment is that in the second embodiment fixing member 30 are provided at both free ends 27 and 35 of the housing 3, whereas in the previous embodiment of FIGS. 1 to 7 included the fixing member 30 are provided only at one longitudinal free end 35 of the housing 3.

The fixing member 30 are again formed by hooks or clips 34, both of which, as in the previous case, extend upwards in a direction away from the convex side 4 of the housing 3.

The front side 7 and the back side 8 of the wearable measuring device 1 are both identically configured in the embodiment of FIGS. 9 to 13 included, and in particular both are of a linear or substantially linear design.

Also, in this embodiment there is no longer really a front side 7 and a back side 8, since the wearable measuring device 1 is symmetrical, so that at a rotation of 180° around an axis AA' perpendicular to the convex side 4 through its center, exactly the same situation is obtained.

FIGS. 15 to 19 show a third possible embodiment of a wearable measuring device 1 according to the present disclosure, which is again intended to be attached to the watch strap 31 of the watch 32.

In the third embodiment fixing member 30 are provided at both the free ends 27 and 35 of the housing 3.

However, in this case, these fixing member 30 extend sideways from the housing 3, in particular sideways from one longitudinal side 36 of this housing 3 at the level of the bottom 17 or the concave side 5 of the housing 3.

At the free end 35, the fixing member 30 are again formed of a kind of hook or clips 34 intended to partially encase the watch strap 31.

At the other free end 27, the fixing member 30 are formed solely by a flat, laterally extending protrusion 37, which is intended to be inserted between the watch strap 31 and the skin 11 of the user in order to hold the wearable measuring device 1 correctly against the skin 11.

It is clear that in this embodiment, the wearable measuring device 1, after attaching it to the watch strap 31, is located next to this watch strap 31 and is being held against the skin 11 there by the fixing member 30.

An aspect of this embodiment is that, when worn, the parts of the wearable measuring device 1 located between the watch strap 31 and the skin 1, in particular a part of the hook or clip 34 and the flat protrusion 37, are not or hardly noticeable to the user due to their small thicknesses T☐ and T, respectively.

However, this embodiment can only be worn in a slightly less discrete manner than in the previous embodiments.

Indeed, in the previous cases, the wearable measuring device 1 is situated entirely between the watch strap 31 and the skin 11 while wearing it, whereas in the case of FIGS. 15 to 19, the wearable measuring device 1 is situated next to the watch strap 31 while wearing it.

FIGS. 20 to 24 show a fourth embodiment of a wearable measuring device 1 according to the present disclosure, which is again intended to be attached to the watch strap 31 of the watch 32.

In this case, however, the fixing member 30 are formed by a flexible strap 38.

The flexible strap 38 is securely attached at one end 39 to the housing 3 of the wearable measuring device 1, in particular at the free end 35 of the housing 3, and the flexible strap 38 extends in line with the length of this elongated housing 3.

At its other free end 40, the flexible strap 38 is equipped with a ring-shaped element 41 to enclose part of the garment or accessory to which the wearable measuring device 1 is to be attached.

In this case, this ring-shaped element 41 is intended to enclose the watch strap 31, in particular in a spot at a certain distance from the housing 3, in accordance with the length of the flexible strap 38.

The flexible strap 38 has a width F corresponding to the width B of the housing 3 as well as to the width of the watch strap 31.

It is clear that this embodiment of the wearable measuring device 1 according to the present disclosure can be worn again in a more discrete manner, just as in the first two embodiments discussed, wherein the wearable measuring device 1 is situated between the watch strap 31 and the skin 11 while wearing it.

Figure 25:
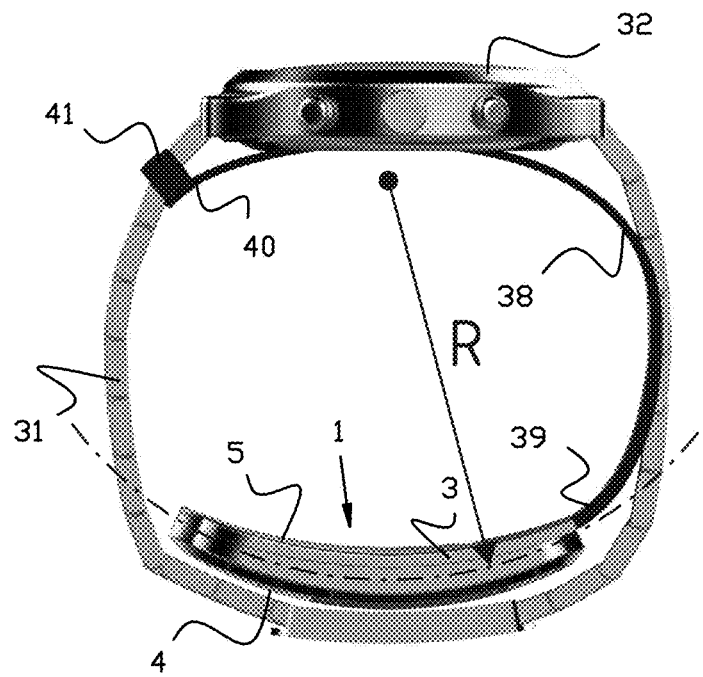
FIG. 25 shows a side view illustrating the use of the wearable measuring device in the embodiment according to FIG. 20.

This is illustrated in FIG. 25.

Figure 26:
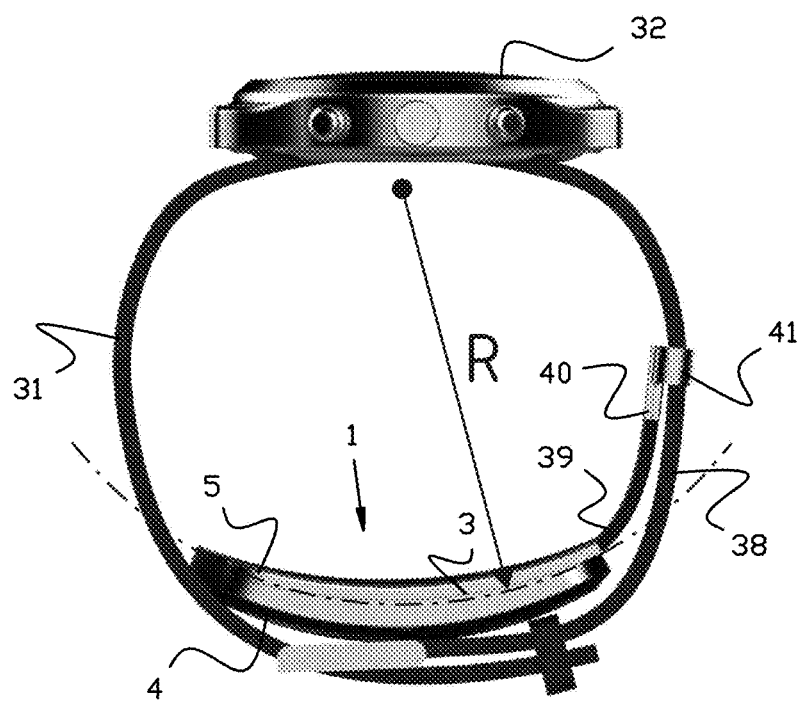
FIG. 26 shows a side view illustrating the use of a wearable measuring device in a modified embodiment compared to the fourth embodiment.

FIG. 26 shows the use of a wearable measuring device 1 according to the present disclosure in a modified fourth embodiment, wherein this time the length of the flexible strap 38 has been shortened compared to the fourth embodiment shown in FIGS. 20 to 25.

In particular, in the illustration of FIG. 25 the length of the flexible strap 38 in the fourth embodiment is substantially larger than half the length of the watch strap 31, whereas in the illustration of FIG. 26 this length is substantially shorter than half the length of the watch strap 31.

In another embodiment of a wearable measuring device 1 according to the present disclosure, which is not further shown in the figures, the fixing member 30 comprise a closing member for closing and re-opening the fixing member 30, respectively during the attachment and the release of the fixing member 30.

Another aspect of the present disclosure is that a central part of the shell-shaped housing 3 is made of a rigid material that is little or not deformable and at least one of the free ends 27 and 35 is made of a more deformable and flexible material that allows the housing 3 to be deformed at the relevant free ends 27 and/or 35 in order to adapt more easily to local restrictions.

The central part of the shell-shaped housing 3 could be made for example of a rigid plastic and the more deformable and flexible material of the above-mentioned free end 27 or 35 or the abovementioned free ends 27 and 35 could be, for example, a silicone.

In some embodiments, the fixing member 30 should be provided at one free end 27 or 35 which is made of a flexible material and/or which is flexibly connected to the more rigid central section of the shell-shaped housing 3.

The result is that the orientation and/or positioning of the more rigid central part of the shell-shaped housing 3 experiences more freedom. In other words, wearing the wearable measuring device 1 becomes more pleasant.

The present disclosure is not limited to the embodiments of a wearable measuring device 1 according to the present disclosure described by way of example and illustrated by the figures; on the contrary, such a wearable measuring device 1 can be achieved in other ways while still remaining within the scope of the present disclosure.

The invention claimed is:

1. A wearable measuring device configured to be worn on a person's body and to measure parameters on the person's skin, the wearable measuring device comprising:
    a measuring block having an elongated curved housing with a convex side and a concave side, a surface of the concave side being equipped with at least two electronic sensors configured to be put in contact with the person's skin on an inside of a wrist of the person's body so as to measure the parameters,
    wherein the wearable measuring device does not have a wristband,
    wherein the measuring block is provided with a fixing member having at least one of hooks or clips, the hooks or clips are configured to be hooked behind or around a part of the wristband to locate the measuring block between the wristband and the person's skin on the inside of the wrist of the person's body,
    wherein the at least two electronic sensors are provided at a mutual distance of at least 20 millimeters from each other, and
    wherein the at least two electronic sensors have a rounded contact surface.

2. The wearable measuring device according to claim 1, wherein the fixing member includes a flexible strap, the flexible strap is fixed at one end to the housing and provided at the other end with a ring-shaped element configured to enclose a part of a garment or an accessory.

3. The wearable measuring device according to claim 1, wherein the fixing member is provided at one longitudinal free end of the housing.

4. The wearable measuring device according to claim 1, wherein the fixing member is provided at both free ends of the housing.

5. The wearable measuring device according to claim 1, wherein two electrical contacts are provided within recesses at one longitudinal free end of the housing, the two electrical contacts are configured to charge a battery inside the housing, and
    wherein the recesses in the housing having rounded edges.

6. The wearable measuring device according to claim 1, wherein the housing has a constant width and a constant thickness over most of a length of the housing.

7. The wearable measuring device according to claim 1, wherein the housing encloses an internal cavity that houses a printed circuit board and a battery, a first part of the housing containing the convex side forming a tub-shaped element having edges that enclose an opening and a second part of the housing having a shape of a concave lid, the concave lid configured to be fitted into the opening.

8. The wearable measuring device according to claim 7, wherein a resin is provided in a part of the internal cavity of the housing which is not filled with the printed circuit board and the battery.

9. The wearable measuring device according to claim 1, wherein a flexible printed circuit board is provided in the housing.

10. The wearable measuring device according to claim 1, wherein the housing contains a battery.

11. The wearable measuring device according to claim 1, wherein a central part of the housing is made of a rigid material, and
    wherein at least one longitudinal free end of the housing provided and hidden under the wristband while in use, is made of a flexible material and/or is flexibly connected to the central part of the housing so as to allow the housing to be deformed at the at least one longitudinal free end.

12. The wearable measuring device according to claim 11, wherein the fixing member is provided at the one longitudinal free end made of the flexible material and/or flexibly connected to the central part of the housing.

13. The wearable measuring device according to claim 1 further comprising a transmitting device configured to wirelessly transmit data to an output device.

14. The wearable measuring device according to claim 1, wherein the housing has a radius R of between 52 and 62 millimeters.

15. The wearable measuring device according to claim 1, wherein the housing has a radius R of between 54 and 60 millimeters.

16. The wearable measuring device according to claim 1, wherein the housing has a radius R of between 56 and 58 millimeters.

17. The wearable measuring device according to claim 1, wherein the fixing member is a clip configured to be hooked behind or around a part of the wristband.

18. The wearable measuring device according to claim 1, wherein the fixing member is a flexible strap having one end fixed to the housing and a ring-shaped element at the other end, the ring-shaped element configured to enclose a part of a garment or an accessory.

* * * * *